(12) United States Patent (10) Patent No.: US 12,618,849 B2

Yoda (45) Date of Patent: May 5, 2026

(54) PEPTIDE ANALYZING METHOD

(71) Applicant: SHIMADZU CORPORATION, Kyoto (JP)

(72) Inventor: Ritsuko Yoda, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 0 days.

(21) Appl. No.: 16/693,783

(22) Filed: Nov. 25, 2019

(65) Prior Publication Data

US 2021/0156871 A1 May 27, 2021

(51) Int. Cl.
| | |
|---|---|
| *G01N 33/68* | (2006.01) |
| *C07K 1/32* | (2006.01) |
| *C12Q 1/37* | (2006.01) |

(52) U.S. Cl.
CPC .......... *G01N 33/6827* (2013.01); *C07K 1/32* (2013.01); *C12Q 1/37* (2013.01); *G01N 33/6848* (2013.01); *G01N 33/6896* (2013.01); *G01N 2333/4709* (2013.01); *G01N 2800/2821* (2013.01)

(58) Field of Classification Search
CPC .......... G01N 33/6827; G01N 33/6896; G01N 2333/4709; G01N 33/6848; G01N 33/537; G01N 2800/2821; C07K 1/32; C12Q 1/37
See application file for complete search history.

(56) References Cited

U.S. PATENT DOCUMENTS

| | | | |
|---|---|---|---|
| 2011/0166035 A1* | 7/2011 | Kleinschmidt | .... C07K 14/4711 |
| | | | 506/9 |
| 2011/0294138 A1 | 12/2011 | Bateman et al. | |
| 2016/0334420 A1 | 11/2016 | Kaneko | |

FOREIGN PATENT DOCUMENTS

| | | |
|---|---|---|
| JP | 2010-249576 A | 11/2010 |
| JP | 2012-508886 A | 4/2012 |
| JP | 2018-194374 A | 12/2018 |
| WO | WO-2009033743 A1 * | 3/2009 ............. C07K 16/18 |
| WO | 2015/111430 A1 | 7/2015 |

OTHER PUBLICATIONS

Lin D et al. Comparison of protein immunoprecipitation-multiple reaction monitoring with Elisa for assay of biomarker candidates in plasma. J. Proteome Res. 2013, 12, 5996-6003. (Year: 2013).*

Jun Seok Kim, et al., "Detection and quantification of plasma amyloid-β by selected reaction monitoring mass spectrometry", Analytica Chimica Acta, 2014, pp. 1-9, vol. 840.

Naoki Kaneko, et al., "Identification and quantification of amyloid beta-related peptides in human plasma using matrix-assisted laser desorption/ionization time-of-flight mass spectrometry", The Japan Academy, 2014, pp. 104-117, vol. 90.

(Continued)

*Primary Examiner* — Kimberly Ballard

(74) *Attorney, Agent, or Firm* — Sughrue Mion, PLLC

(57) ABSTRACT

In the analysis method according to the present invention, a predetermined peptide is separated by immunoprecipitation using an antibody which specifically binds to either an N-terminus or a C-terminus of the predetermined peptide. The separated predetermined peptide is digested with a protease to prepare peptide fragments, and among the peptide fragments, a peptide fragment at a terminus opposite to a terminus binding to the antibody is mass-spectrometrically detected.

6 Claims, 1 Drawing Sheet

Specification includes a Sequence Listing.

(56) References Cited

OTHER PUBLICATIONS

Tomoyuki OE, et al., "Quantitative analysis of amyloid β peptides in cerebrospinal fluid of Alzheimer's disease patients by immunoaffinity purification and stable isotope dilution liquid chromatography/negative electrospray ionization tandem mass spectrometry", Rapid Communications in Mass Spectrometry, 2006, pp. 3723-3735, vol. 20.

Josef Pannee, et al., "A Selected Reaction Monitoring (SRM)-Based Method for Absolute Quantification of Aβ38, Aβ40, and Aβ42 in Cerebrospinal Fluid of Alzheimer's Disease Patients and Healthy Controls", Journal of Alzheimer's Disease, 2013, pp. 1021-1032, vol. 33.

Mary E. Lame, et al., "Quantitation of amyloid beta peptides Aβ1-38, Aβ1-40, and Aβ1-42 in human cerebrospinal fluid by ultra-performance liquid chromatography-tandem mass spectrometry", Analytical Biochemistry, 2011, pp. 133-139, vol. 419.

Bateman et al., "Human amyloid-β synthesis and clearance rates as measured in cerebrospinal fluid in vivo", Nature Medicine, Jul. 2006, vol. 12, No. 7, pp. 856-861 (total 6 pages).

Communication dated Aug. 11, 2020 from Japanese Patent Office in JP Application No. 2017-096857.

* cited by examiner

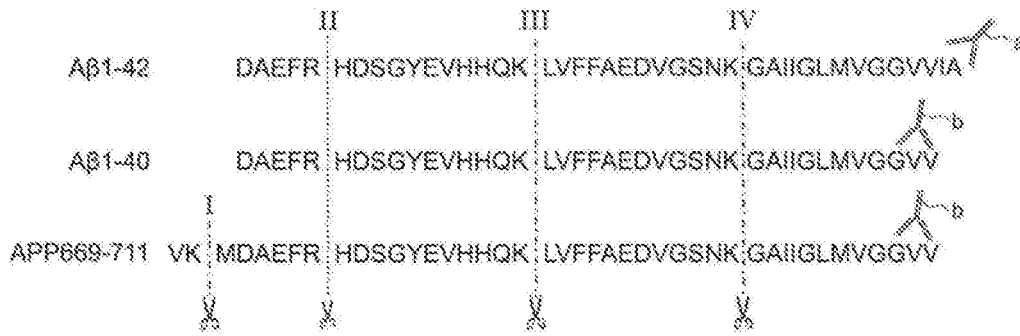

PEPTIDE ANALYZING METHOD

CROSS REFERENCE TO RELATED APPLICATION

This application relates to, but does not claim priority from, JP Ser. No. JP2017-096857 filed on May 15, 2017 and published as JP Pub. No. JP2018-194374 on Dec. 6, 2018, the entire contents of which are incorporated herein fully by reference.

INCORPORATION BY REFERENCE OF SEQUENCE LISTING

The content of the electronically submitted sequence listing, file name: Q250733_substitute sequence listing as filed.txt; size: 9,052 bytes; and date of creation: Dec. 30, 2025, filed herewith, is incorporated herein by reference in its entirety.

BACKGROUND OF THE INVENTION

Field of the Invention

The present invention relates to a peptide analyzing method. More specifically, the present invention relates to a method for mass-spectrometrically identifying and/or quantifying peptides cleaved at different positions by in vivo processing.

Description of the Related Art

Amyloid β (Aβ) is a peptide composed of about 40 amino acid residues and is thought to be deeply involved in development of Alzheimer's disease. It is known that an amyloid precursor protein composed of 770 amino acid residues (APP: SEQ ID NO: 1) is cleaved between Met671 and Asp672 by a β-secretase to cut out a C-terminus-side peptide (APP672-770), and this peptide is cleaved by a γ-secretase to produce Aβ.

Aβ is attracting attention as a biomarker for Alzheimer's disease. Some trials to mass-spectrometrically quantify an amount of Aβ contained in a biological sample have been reported. For example, WO 2015/111430 reports a case that 22 types of APP-cleaved peptides were detected from a trace amount of human plasma by an analysis method of combining immunoprecipitation (IP) using anti-Aβ antibodies which specifically bind to Aβ (6E10 for which Phe4-Gly9 of Aβ is an epitope, and 4G8 for which Leu17-Val24 of Aβ is an epitope) with matrix-assisted laser desorption ionization-mass spectrometry (MALDI-MS). WO 2015/111430 reports a case that a peptide cleaved at an N-terminus side of a site to be cleaved by β-secretase, such as APP669-711 (SEQ ID NO: 5), was detected as a peptide produced by APP processing.

J. S. Kim et al., Analytica Chimica Acta, 2014, 840, 1-9 reports a case that a sample obtained by digesting all proteins in plasma with trypsin was analyzed by multidimensional LC/MS/MS to select Aβ17-28 as a surrogate peptide, and a total Aβ amount was quantified by multiple reaction monitoring (MRM; also referred to as selective reaction monitoring (SRM)).

SUMMARY OF THE INVENTION

In MALDI-MS, a concentration of a specific peptide in a sample can be quantified from a relative ratio of a peak intensity in a mass spectrum, but it cannot be said that MALDI-MS is suitable for quantifying an absolute content of a specific peptide. On the other hand, in MRM, a peptide is detected through MS/MS by selecting a combination of a specific precursor ion and product ion, and therefore MRM has an advantage that a trace amount of sample can be high-sensitively quantified with high selectivity from lots of impurities. In addition, a calibration curve method or an internal standard method enables quantitative analysis with higher accuracy than MALDI-MS.

However, since an intermediate sequence of Aβ is selected as a surrogate peptide in the method described in J. S. Kim et al., Analytica Chimica Acta, 2014, 840, 1-9, Aβ having a different C-terminus cleavage site (e.g., Aβ1-38 (SEQ ID NO: 2), Aβ1-40 (SEQ ID NO: 3), Aβ1-42 (SEQ ID NO: 4), and an APP-cleaved peptide of which an N-terminus side is cleaved at a site other than the β-secretase cleavage site (between Met671 and Asp672 of APP) (e.g., the aforementioned APP669-711)) cannot be individually quantified.

Examples of plural types of peptides produced by cleaving a precursor protein at different cleavage sites with in vivo processing include, besides Aβ produced from APP, a granulin produced from a progranulin, a parathyroid hormone (PTH) produced from a prepro-PTH, a brain natriuretic peptide (BNP) produced from a prepro-BNP, an adrenocorticotropic hormone (ACTH) produced from proopiomelanocortin, an α-melanocyte stimulating hormone (α-MSH), a β-MSH and a γ-MSH.

For pathological diagnosis and the like, there is a need for an analytical technique capable of individually identifying/quantifying plural types of peptides produced by cleaving a precursor protein at different cleavage sites with in vivo processing.

In the analysis method according to the present invention, a peptide is separated by immunoprecipitation (IP) using an antibody which specifically binds to either an N-terminus or C-terminus of a predetermined peptide such as an APP-cleaved peptide (e.g., Aβ). The peptide separated by IP is digested with a protease to prepare peptide fragments, and among the peptide fragments, a peptide fragment at a terminus opposite to a terminus binding to the antibody is mass-spectrometrically detected. The peptide fragments may also be mass-spectrometrically analyzed by multiple reaction monitoring (MRM).

In the method according to the present invention, either an N-terminus or C-terminus of a peptide is discriminated by IP using an antibody, and the other N-terminus or C-terminus is mass-spectrometrically discriminated, and therefore it is possible to individually detect and quantify peptides having different cleavage sites.

BRIEF DESCRIPTION OF THE DRAWING

FIG. 1 is a schematic diagram illustrating capture of APP-cleaved peptides by antibodies, and positions to be cleaved by a protease (Aβ1-42: SEQ ID NO: 4; Aβ1-40: SEQ ID NO: 3; and APP669-711: SEQ ID NO: 5).

DETAILED DESCRIPTION OF THE PREFERRED EMBODIMENTS

In the analysis method according to the present invention, either an N-terminus or a C-terminus of a peptide is discriminated by an antibody and the peptide is separated by immunoprecipitation (IP). The peptide separated by IP is digested with a protease to produce peptide fragments, and then a peptide fragment including a terminus opposite to an antibody-discriminating site (epitope) is mass-spectrometrically analyzed. In this method, one terminus of the peptide is discriminated by an antibody, and the other terminus of the peptide is mass-spectrometrically discriminated, and therefore plural types of peptides produced by cleavage at plural positions in vivo can be detected and quantified for each amino acid sequence.

The peptides to be analyzed are not particularly limited, but the method according to the present invention is suitable for analyzing plural types of peptides produced by cleavage at different sites in vivo processing. Examples of a precursor protein which produce plural types of peptides include amyloid precursor protein (APP), progranulin, prepro-PTH, prepro-BNP, and proopiomelanocortin. Hereinafter, analysis of peptides (APP-cleaved peptides) produced by processing APP will be mainly described.

[Separation of Peptide by Immunoprecipitation]

First, a predetermined peptide is separated and recovered from a biological sample by immunoprecipitation. Examples of the biological sample include blood sample, cerebrospinal fluid (CSF), urine, and body fluids such as body secretion, saliva and sputum, and feces. Examples of the blood sample include whole blood, plasma, and serum. The blood sample may be prepared by appropriately treating whole blood collected from a living body. For example, when an APP-cleaved peptide is analyzed, a biological sample for screening Alzheimer's disease or other diseases is a sample to be analyzed.

The biological sample is brought into contact with an antibody, so that a predetermined peptide in the biological sample specifically binds to the antibody. As the antibody, an antibody which recognizes and specifically binds to a peptide to be detected is used. As an antibody having an antigen-binding site capable of recognizing the APP-cleaved peptide, various anti-amyloid β antibodies can be used.

The present invention uses an antibody for which an amino acid sequence at an N-terminus side or a C-terminus side of the APP-cleaved peptide is an epitope. The antibody may be either monoclonal or polyclonal. The antibody only needs to contain an antigen-binding site, and may be an antibody fragment (domain) such as $F(ab')_2$, F(ab'), F(ab), Fd or Fv. An antibody fragment containing no Fc domain such as F(ab'), F(ab) and Fv is preferable because of high binding specificity.

As an antibody for which an N-terminus side of Aβ is an epitope, 3D6 (epitope: Aβ1-5), pAb-EL16 (epitope: Aβ1-7), 2H4 (epitope: Aβ1-8), 1E11 (epitope: Aβ1-8) 20.1 (epitope: Aβ1-10), pAb1-42 (epitope: Aβ1-11), NAB228 (epitope: Aβ1-11), rabbit anti-Aβ polyclonal antibody (Abcam) (epitope: Aβ1-14), Aβ10 (epitope: Aβ1-16), 82E1 (epitope: Aβ1-16), DE2 (epitope: Aβ1-16), DE2B4 (epitope: Aβ1-17), rabbit anti-human Aβ polyclonal antibody (ABR) (epitope: N-terminus of Aβ), and the like are known.

As an antibody for which an C-terminus side of Aβ is an epitope, G2-10 (epitope: Aβ31-40), 1A10 (epitope: Aβ35-40), EP1876Y (epitope: Aβx-40), G2-11 (epitope: Aβ33-42), 16C11 (epitope: Aβ33-42), 21F12 (epitope: Aβ34-42), D-17 goat anti-Aβ antibody (epitope: C-terminus of Aβ1-42), BC05 (epitope: C-terminus of Aβ1-42), and the like are known.

These antibodies may be used in combination of two or more types for the purpose of improving a peptide collection efficiency. In addition, an antibody for which an intermediate sequence of Aβ is an epitope may be used in combination. As the antibody for which the intermediate sequence of Aβ is an epitope, 10D5 (epitope: Aβ3-7), 6E10 (epitope: Aβ4-9), WO-2 (epitope: Aβ4-10), 1A3 (epitope: Aβ5-9), pAb-EL21 (epitope: Aβ5-11), 310-0 (epitope: Aβ5-16), chicken anti-human Aβ polyclonal antibody (Abcam) (epitope: Aβ12-28 or Aβ25-35), 12C3 (epitope: Aβ10-16), 16C9 (epitope: Aβ10-16), 19B8 (epitope: Aβ9-10), pAb-EL26 (epitope: Aβ11-26), BAM90.1 (epitope: Aβ13-28), rabbit anti-Aβ polyclonal antibody (MBL) (epitope: Aβ15-30), 22D12 (epitope: Aβ18-21), 266 (epitope: Aβ16-24), pAb-EL17 (epitope: Aβ15-24), 4G8 (epitope: Aβ17-24), rabbit anti-Aβ polyclonal antibody (Abcam) (epitope: Aβ22-35), and the like are known.

The antibody may be immobilized on any carrier. Examples of the carrier used for immobilizing the antibody include agarose, sepharose, dextran, silica gel, polyacrylamide, polystyrene, polyethylene, polypropylene, polyester, polyacrylonitrile, (meth)acrylic acid-based polymer, fluoresin, metal complex resin, glass, and metal. The antibody may be bound to the carrier via a spacer.

IP using the aforementioned antibodies can be performed by a known method. For example, when using an antibody immobilized on a carrier, it is preferable that a peptide to be analyzed is bound to the antibody on the surface of the carrier, components not binding to the antibody are washed away, then the peptide is dissociated from the antibody, and an eluent is recovered.

The biological sample may be pretreated before binding the antibody to the peptide in the biological sample. For example, the biological sample is brought into contact with a carrier to which a protein G, a protein A or the like is bound, to remove antibodies such as IgG and IgM contained in blood and the like, thereby non-specific adsorption with the peptide to be analyzed such as Aβ can be suppressed, and binding specificity between the AR-specific binding antibody and the peptide to be analyzed can be enhanced to improve quantitativity of the analysis.

As a solution for binding the antibody and the peptide, a buffer solution at pH about 6.5 to 8.5 containing a surfactant is preferably used for suppressing non-specific adsorption. The surfactant is preferably a surfactant which hardly denature proteins such as antibodies and is easy to remove by washing, such as a neutral surfactant having maltose on a hydrophilic moiety, a neutral surfactant having trehalose on a hydrophilic moiety, and a neutral surfactant having glucose on a hydrophilic moiety. As for the composition of the buffer solution, a Tris buffer, a phosphate buffer, a HEPES buffer, or the like can be used.

After binding the antibody and the peptide, impurities not binding to the antibody are removed. When using an antibody immobilized on a carrier, impurities may be removed by washing with a washing solution. For example, it is preferable to perform washing with an aqueous solution containing ammonium ions after washing with a neutral buffer solution containing a surfactant.

After washing, the peptide is dissociated from the antibody to separate and recover the peptide. For example, a carrier surface to which an antibody is immobilized is brought into contact with an eluent, so that a peptide is dissociated from the antibody, and the dissociated peptide is eluted. As the eluent, an acidic aqueous solution at pH about 1 to 4 is generally used. The eluent may contain an organic solvent such as acetonitrile, acetone, methanol, ethanol, isopropanol, and chloroform.

[Protease Treatment and Mass Spectrometry]

The peptide separated by immunoprecipitation is fragmented by protease digestion. Generally, prior to protease treatment, the peptide is modified and alkylated. Conditions for the modification and alkylation are not particularly limited, and known conditions are appropriately adopted.

Conditions for the protease treatment are not particularly limited, and an appropriate protocol is adopted depending on a protease for use. For example, it is preferable to incubate the peptide in a buffer solution adjusted to approximately an optimum pH for the protease generally at about 37° C. for about 4 to 20 hours.

The protease recognizes amino acid sequences and selectively cleaves specific bonds in specific sequences. As the protease, trypsin (cleavage position: C-terminus side of a basic amino acid residue (Arg and Lys)), Lys-C (cleavage position: C-terminus side of Lys), arginine endopeptidase (cleavage position: C-terminus side of Arg), chymotrypsin (cleavage position: C-terminus side of an aromatic amino acid (Phe, Tyr and Trp)), pepsin (cleavage position: N-terminus side of an aromatic (Phe, Tyr and Trp)), Asn-C (cleavage position: C-terminus side of Asn), and the like are used.

It is preferable to select a protease so that a fragment having an amino acid sequence specific to the peptide to be analyzed can be obtained. Two or more types of proteases may be used in combination. When detecting a peptide fragment by MRM, it is preferable that a peptide fragment composed of 6 or more amino acid residues is used as a precursor ion to be detected, from the viewpoint of ensuring specificity. An upper limit of a length of the peptide fragment is not particularly limited, but a number of amino acid residues is preferably 30 or less because of easy ionization.

FIG. 1 is a schematic diagram illustrating capture of peptides by immunoprecipitation using antibodies which specifically bind to the C-terminus sides of three types of APP-cleaved peptides, and peptide cleavage positions to be cleaved by a protease. The cleavage positions I to IV in the FIGURE are cleavage positions to be cleaved by trypsin (C-terminus sides of Lys residue and Arg residue). The cleavage position II indicated by the dashed line in the FIGURE is at the C-terminus side of the Arg residue, and is cleaved by trypsin but not by Lys-C.

When performing IP with an antibody (a) for which a C-terminus of Aβ1-42 is an epitope, only Aβ1-42 having Ala42 at the C-terminus is captured among the three types of peptides presented in FIG. 1. The peptide captured by IP using the antibody (a) is digested with trypsin, then a peptide fragment having a sequence "DAEFR" (SEQ ID NO: 8) at an N-terminus side of cleavage site II is mass-spectrometrically detected, and thereby the presence of Aβ1-42 can be confirmed. Also by trypsin digestion of Aβ1-40, the peptide fragment having the sequence "DAEFR" (SEQ ID NO: 8) is produced, but, by IP with the antibody (a), Aβ40 is not captured, and therefore only the peptide fragment derived from Aβ1-42 is detected.

When the peptide captured by IP using the antibody (a) is digested with Lys-C, if a peptide fragment having a sequence "DAEFRHDSGYEVHHQK" (SEQ ID NO: 6) at an N-terminus side of cleavage site III can be mass-spectrometrically detected, the presence of Aβ1-42 can be confirmed. When using trypsin, a number of amino acid residues in an N-terminus side peptide fragment produced from Aβ1-42 is as small as 5, whereas when using Lys-C, a peptide fragment having 16 amino acid residues is obtained, and therefore Lys-C is suitable for detection and quantitation of the peptide fragment by MRM.

When performing IP with an antibody (b) for which a C-terminus of Aβ1-40 is an epitope, two types, Aβ1-40 and APP669-711 are captured among the three types of peptides presented in FIG. 1. Aβ1-42 is captured by IP using the antibody (a), and the solution which has flowed out without being captured by the antibody (a) (including lavage) may be subjected to IP using the antibody (b) to capture Aβ1-40 and APP669-711.

From a sample obtained by digesting a peptide captured by IP using the antibody (b) with Lys-C, a peptide having the sequence "DAEFRHDSGYEVHHQK" (SEQ ID NO: 6) at the N-terminus side of cleavage position III of Aβ1-40, and a peptide having the sequence "MDAE-FRHDSGYEVHHQK" (SEQ ID NO: 7) at the N-terminus side of cleavage position III (sequence between cleavage position I and cleavage position III) of APP669-711 are produced. Since these peptides have different molecular weights, it is possible to mass-spectrometrically distinguish between these peptides.

Although it is impossible to discriminate between Aβ1-40 and APP669-711 which share the same C-terminus sequences only by IP using the antibody (b), it is possible to identify difference in the N-terminus side sequence (difference in the cleavage site from the APP in the living body) by separating a peptide by IP using the C-terminus side as an antibody-discriminating site, and selecting, as a transition, a protease-digested fragment at the N-terminus side of the peptide captured and recovered by IP.

In the present invention, the peptide is separated by IP using the antibody which specifically binds to either the C-terminus or N-terminus of the peptide as described above, and then the peptide fragment at the terminus opposite to the antibody binding site is analyzed. For example, for a peptide separated by IP using an antibody which binds to a C-terminus side of Aβ, after protease treatment, a protease-digested fragment at an N-terminus side is selected as a subject to be mass-spectrometrically detected. For the peptide captured by IP using the antibody which binds to the N-terminus side of Aβ, the protease-digested fragment at the C-terminus side is mass-spectrometrically analyzed. For the three types of peptides presented in FIG. 1, Aβ1-42 and Aβ1-40 can be separated from APP669-711 by IP at the C-terminus side, and Aβ1-42 can be discriminated from Aβ1-40 by mass spectrometry of the peptide fragment at the N-terminus.

In protease digestion after IP, it is preferable to select a protease so that the number of the amino acid residues in the peptide fragment to be detected is within the aforementioned range. When discriminating the C-terminus side of Aβ by IP and mass-spectrometrically discriminating the N-terminus side of Aβ, the number of the amino acid residues in the trypsin-digested fragment at the N-terminus is 5, and the number of the amino acid residues in the Lys-C-digested fragment is 16. It can be said that Lys-C is suitable as a protease for obtaining an N-terminus peptide fragment having a length suitable for analysis using MRM.

The protease-treated sample may be subjected to treatments such as desalination, solubilization, condensation, and drying, as necessary. For example, desalination and condensation may be performed using a spin column for solid phase extraction, or the like.

The peptide fragment obtained by protease treatment are analyzed by a mass spectrometer. The peptide fragment can be analyzed by various mass spectrometry methods, but analysis using multiple reaction monitoring (MRM) is preferable because of high selectivity and sensitivity. In MRM, before a sample is introduced into the mass spectrometer, the sample is subjected to liquid chromatography (LC) separation.

The sample introduced into the mass spectrometer is ionized by an ionization probe. Ions (precursor ions) derived from the peptide fragment to be detected are selected by the previous mass spectrometry. The precursor ions are cleaved into plural types of ions (product ions) by CID or the like, and specific product ions are separated based on an m/z by subsequent mass spectrometry, and detected by a detector. In MRM, a combination of an m/z of precursor ions produced from the peptide to be analyzed with an m/z of product ions selected by the subsequent mass spectrometry of each precursor ion is predetermined.

As an example, MRM transitions of the peptide having the sequence "DAEFRHDSGYEVHHQK" (SEQ ID NO: 6) at the N-terminus side of the Lys-C-digested Aβ1-42 (also applies to the Lys-C-digested Aβ1-40) are presented below.

TABLE 1

| Precursor ion | | Product ion | | | |
| --- | --- | --- | --- | --- | --- |
| | | Ion | | | Collision |
| m/z | Charge | m/z | species | Charge | energy (V) |
| 489.75 | 4+ | 590.65 | y14 | 3+ | −18 |
| 489.75 | 4+ | 485.25 | b16 | 4+ | −18 |
| 489.75 | 4+ | 547.6 | y13 | 3+ | −18 |

A content (concentration) of a predetermined peptide in a biological sample such as blood can be calculated based on an amount of the product ions detected by MRM. The amount of the product ions is previously correlated to the concentration of the peptide in the biological sample by predetermined parameters. A method for correlating the amount of the product ions with the concentration of the peptide is e.g. a method using a standard curve (calibration curve) based on an external standard. The standard curve can be obtained by analyzing a peptide fragment (external standard) having a known concentration under the same conditions as for this analysis (analysis of the biological sample), and plotting concentrations and peak areas (or peak intensities) of product ions.

What is claimed is:

1. A peptide analyzing method comprising:

separating Aβ1-42 from Aβ1-40 and APP669-711 by immunoprecipitation using an antibody which specifically binds to a C-terminus of Aβ1-42, or separating Aβ1-40 and APP669-711 from Aβ1-42 by immunoprecipitation using an antibody which specifically binds to a C-terminus of Aβ1-40 or APP669-711;

preparing peptide fragments by digesting with a protease Aβ1-40 and APP669-711 separated; and mass-spectrometrically detecting, among the peptide fragments, a peptide fragment at the N-terminus of Aβ1-40 and APP669-711.

2. The peptide analyzing method according to claim 1, wherein the peptide fragments are detected by multiple reaction monitoring.

3. The peptide analyzing method according to claim 1, wherein the protease is trypsin.

4. The peptide analyzing method according to claim 1, wherein the protease is Lys-C.

5. A method for analyzing peptides, comprising:

preparing a biological sample containing plural types of peptides produced by cleaving a precursor protein at different cleavage sites with in vivo processing, wherein the plural types of peptides are generated from an amyloid precursor protein (APP);

contacting the biological sample with an antibody that specifically binds to a C-terminus of Aβ1-42;

separating, by immunoprecipitation, peptides that are bound to the antibody from those that are not bound to the antibody, among the plural types of peptides;

digesting the separated peptides with an enzyme to obtain peptide fragments;

analyzing the obtained peptide fragments by mass spectrometry; and based on the results of the mass spectrometry, making the following determinations: I) determining that an ion derived from a peptide fragment that has a sequence at an N-terminus corresponding to an N-terminus side of Aβ1-40 detected in the mass spectrometry is an ion derived from peptide fragment generated from Aβ1-40 present in the biological sample by the enzyme digestion, rather than an ion derived from peptide fragments generated from Aβ1-42 present in the biological sample by the enzyme digestion; and II) determining that an ion derived from peptide fragments that has a sequence at an N-terminus corresponding to an N-terminus side of APP669-711 detected in the mass spectrometry is an ion derived from peptide fragment generated from APP669-711 present in the biological sample, generated by the enzyme digestion.

6. A method for analyzing peptides, comprising:

preparing a biological sample containing plural types of peptides, wherein the plural types of peptides are generated from the amyloid precursor protein (APP) being cleaved at different sites due to in vivo processing;

contacting the biological sample with an antibody that specifically binds to a C-terminus of Aβ1-40 or APP669-711;

separating, by immunoprecipitation, peptides that are bound to the antibody from those that are not bound to the antibody, among the plural types of peptides;

digesting the separated peptides with an enzyme to obtain peptide fragments;

analyzing the obtained peptide fragments by mass spectrometry; and based on the results of the mass spectrometry, making the following determinations: I) determining that an ion derived from a peptide fragment that has a sequence at an N-terminus corresponding to an N-terminus side of Aβ1-40 detected in the mass spectrometry is an ion derived from a peptide fragment generated from Aβ1-40 present in the biological sample by the enzyme digestion, rather than an ion derived from peptide fragments generated from Aβ1-42 present in the biological sample by the enzyme digestion; and II) determining that an ion derived from peptide fragments that has a sequence at an N-terminus corresponding to an N-terminus side of APP669-711 detected in the mass spectrometry is an ion derived from a peptide fragment generated from APP669-711 present in the biological sample, generated by the enzyme digestion.

* * * * *

SEQUENCE LISTING

<160> NUMBER OF SEQ ID NOS: 8

<210> SEQ ID NO 1
<211> LENGTH: 770
<212> TYPE: PRT
<213> ORGANISM: Homo sapiens

<400> SEQUENCE: 1

```
Met Leu Pro Gly Leu Ala Leu Leu Leu Leu Ala Ala Trp Thr Ala Arg
1               5                   10                  15

Ala Leu Glu Val Pro Thr Asp Gly Asn Ala Gly Leu Leu Ala Glu Pro
            20                  25                  30

Gln Ile Ala Met Phe Cys Gly Arg Leu Asn Met His Met Asn Val Gln
        35                  40                  45

Asn Gly Lys Trp Asp Ser Asp Pro Ser Gly Thr Lys Thr Cys Ile Asp
    50                  55                  60

Thr Lys Glu Gly Ile Leu Gln Tyr Cys Gln Glu Val Tyr Pro Glu Leu
65                  70                  75                  80

Gln Ile Thr Asn Val Val Glu Ala Asn Gln Pro Val Thr Ile Gln Asn
            85                  90                  95

Trp Cys Lys Arg Gly Arg Lys Gln Cys Lys Thr His Pro His Phe Val
            100                 105                 110

Ile Pro Tyr Arg Cys Leu Val Gly Glu Phe Val Ser Asp Ala Leu Leu
        115                 120                 125

Val Pro Asp Lys Cys Lys Phe Leu His Gln Glu Arg Met Asp Val Cys
        130                 135                 140

Glu Thr His Leu His Trp His Thr Val Ala Lys Glu Thr Cys Ser Glu
145                 150                 155                 160

Lys Ser Thr Asn Leu His Asp Tyr Gly Met Leu Leu Pro Cys Gly Ile
                165                 170                 175

Asp Lys Phe Arg Gly Val Glu Phe Val Cys Cys Pro Leu Ala Glu Glu
            180                 185                 190

Ser Asp Asn Val Asp Ser Ala Asp Ala Glu Glu Asp Asp Ser Asp Val
            195                 200                 205
```

Trp Trp Gly Gly Ala Asp Thr Asp Tyr Ala Asp Gly Ser Glu Asp Lys
    210             215             220

Val Val Glu Val Ala Glu Glu Glu Val Ala Glu Val Glu Glu Glu
225             230             235             240

Glu Ala Asp Asp Asp Glu Asp Asp Glu Asp Gly Asp Glu Val Glu Glu
            245             250             255

Glu Ala Glu Glu Pro Tyr Glu Glu Ala Thr Glu Arg Thr Thr Ser Ile
            260             265             270

Ala Thr Thr Thr Thr Thr Thr Thr Glu Ser Val Glu Glu Val Val Arg
        275             280             285

Glu Val Cys Ser Glu Gln Ala Glu Thr Gly Pro Cys Arg Ala Met Ile
        290             295             300

Ser Arg Trp Tyr Phe Asp Val Thr Glu Gly Lys Cys Ala Pro Phe Phe
305             310             315             320

Tyr Gly Gly Cys Gly Gly Asn Arg Asn Asn Phe Asp Thr Glu Glu Tyr
            325             330             335

Cys Met Ala Val Cys Gly Ser Ala Met Ser Gln Ser Leu Leu Lys Thr
            340             345             350

Thr Gln Glu Pro Leu Ala Arg Asp Pro Val Lys Leu Pro Thr Thr Ala
        355             360             365

Ala Ser Thr Pro Asp Ala Val Asp Lys Tyr Leu Glu Thr Pro Gly Asp
    370             375             380

Glu Asn Glu His Ala His Phe Gln Lys Ala Lys Glu Arg Leu Glu Ala
385             390             395             400

Lys His Arg Glu Arg Met Ser Gln Val Met Arg Glu Trp Glu Glu Ala
            405             410             415

Glu Arg Gln Ala Lys Asn Leu Pro Lys Ala Asp Lys Lys Ala Val Ile
            420             425             430

Gln His Phe Gln Glu Lys Val Glu Ser Leu Glu Gln Glu Ala Ala Asn
        435             440             445

Glu Arg Gln Gln Leu Val Glu Thr His Met Ala Arg Val Glu Ala Met
    450             455             460

Leu Asn Asp Arg Arg Arg Leu Ala Leu Glu Asn Tyr Ile Thr Ala Leu
465             470             475             480

Gln Ala Val Pro Pro Arg Pro Arg His Val Phe Asn Met Leu Lys Lys
            485             490             495

Tyr Val Arg Ala Glu Gln Lys Asp Arg Gln His Thr Leu Lys His Phe
            500             505             510

Glu His Val Arg Met Val Asp Pro Lys Lys Ala Ala Gln Ile Arg Ser
        515             520             525

Gln Val Met Thr His Leu Arg Val Ile Tyr Glu Arg Met Asn Gln Ser
    530             535             540

Leu Ser Leu Leu Tyr Asn Val Pro Ala Val Ala Glu Glu Ile Gln Asp
545             550             555             560

Glu Val Asp Glu Leu Leu Gln Lys Glu Gln Asn Tyr Ser Asp Asp Val
            565             570             575

Leu Ala Asn Met Ile Ser Glu Pro Arg Ile Ser Tyr Gly Asn Asp Ala
            580             585             590

Leu Met Pro Ser Leu Thr Glu Thr Lys Thr Thr Val Glu Leu Leu Pro
        595             600             605

Val Asn Gly Glu Phe Ser Leu Asp Asp Leu Gln Pro Trp His Ser Phe
    610             615             620

-continued

```
Gly Ala Asp Ser Val Pro Ala Asn Thr Glu Asn Glu Val Glu Pro Val
625             630             635             640

Asp Ala Arg Pro Ala Ala Asp Arg Gly Leu Thr Thr Arg Pro Gly Ser
                645             650             655

Gly Leu Thr Asn Ile Lys Thr Glu Glu Ile Ser Glu Val Lys Met Asp
                660             665             670

Ala Glu Phe Arg His Asp Ser Gly Tyr Glu Val His His Gln Lys Leu
            675             680             685

Val Phe Phe Ala Glu Asp Val Gly Ser Asn Lys Gly Ala Ile Ile Gly
        690             695             700

Leu Met Val Gly Gly Val Val Ile Ala Thr Val Ile Val Ile Thr Leu
705             710             715             720

Val Met Leu Lys Lys Lys Gln Tyr Thr Ser Ile His His Gly Val Val
                725             730             735

Glu Val Asp Ala Ala Val Thr Pro Glu Glu Arg His Leu Ser Lys Met
                740             745             750

Gln Gln Asn Gly Tyr Glu Asn Pro Thr Tyr Lys Phe Phe Glu Gln Met
            755             760             765

Gln Asn
    770

<210> SEQ ID NO 2
<211> LENGTH: 38
<212> TYPE: PRT
<213> ORGANISM: Homo sapiens

<400> SEQUENCE: 2

Asp Ala Glu Phe Arg His Asp Ser Gly Tyr Glu Val His His Gln Lys
1               5               10              15

Leu Val Phe Phe Ala Glu Asp Val Gly Ser Asn Lys Gly Ala Ile Ile
            20              25              30

Gly Leu Met Val Gly Gly
        35

<210> SEQ ID NO 3
<211> LENGTH: 40
<212> TYPE: PRT
<213> ORGANISM: Homo sapiens

<400> SEQUENCE: 3

Asp Ala Glu Phe Arg His Asp Ser Gly Tyr Glu Val His His Gln Lys
1               5               10              15

Leu Val Phe Phe Ala Glu Asp Val Gly Ser Asn Lys Gly Ala Ile Ile
            20              25              30

Gly Leu Met Val Gly Gly Val Val
        35              40

<210> SEQ ID NO 4
<211> LENGTH: 42
<212> TYPE: PRT
<213> ORGANISM: Homo sapiens

<400> SEQUENCE: 4

Asp Ala Glu Phe Arg His Asp Ser Gly Tyr Glu Val His His Gln Lys
1               5               10              15

Leu Val Phe Phe Ala Glu Asp Val Gly Ser Asn Lys Gly Ala Ile Ile
            20              25              30

Gly Leu Met Val Gly Gly Val Val Ile Ala
```

-continued

```
                35                      40

<210> SEQ ID NO 5
<211> LENGTH: 43
<212> TYPE: PRT
<213> ORGANISM: Homo sapiens

<400> SEQUENCE: 5

Val Lys Met Asp Ala Glu Phe Arg His Asp Ser Gly Tyr Glu Val His
1               5                   10                  15

His Gln Lys Leu Val Phe Phe Ala Glu Asp Val Gly Ser Asn Lys Gly
            20                  25                  30

Ala Ile Ile Gly Leu Met Val Gly Gly Val Val
            35                  40

<210> SEQ ID NO 6
<211> LENGTH: 16
<212> TYPE: PRT
<213> ORGANISM: Homo sapiens

<400> SEQUENCE: 6

Asp Ala Glu Phe Arg His Asp Ser Gly Tyr Glu Val His His Gln Lys
1               5                   10                  15

<210> SEQ ID NO 7
<211> LENGTH: 17
<212> TYPE: PRT
<213> ORGANISM: Homo sapiens

<400> SEQUENCE: 7

Met Asp Ala Glu Phe Arg His Asp Ser Gly Tyr Glu Val His His Gln
1               5                   10                  15

Lys

<210> SEQ ID NO 8
<211> LENGTH: 5
<212> TYPE: PRT
<213> ORGANISM: Homo sapiens

<400> SEQUENCE: 8

Asp Ala Glu Phe Arg
1               5
```